United States Patent
Vora et al.

(10) Patent No.: US 8,148,105 B2
(45) Date of Patent: Apr. 3, 2012

(54) SCALEABLE MANUFACTURING PROCESS FOR CYSTEINE ENDOPROTEASE B, ISOFORM 2

(75) Inventors: Harmit Vora, South San Francisco, CA (US); James McIntire, Castro Valley, CA (US); Pawan Kumar, Mountain View, CA (US); Chaitan Khosla, Palo Alto, CA (US)

(73) Assignees: The Board of Trustees of the Leland Stanford Junior University, Palo Alto, CA (US); Alvine Pharmaceuticals, Inc., San Carlos, CA (US)

( * ) Notice: Subject to any disclaimer, the term of this patent is extended or adjusted under 35 U.S.C. 154(b) by 0 days.

(21) Appl. No.: 12/531,037

(22) PCT Filed: Mar. 14, 2008

(86) PCT No.: PCT/US2008/003425
§ 371 (c)(1),
(2), (4) Date: Apr. 21, 2010

(87) PCT Pub. No.: WO2008/115428
PCT Pub. Date: Sep. 25, 2008

(65) Prior Publication Data
US 2010/0196955 A1 Aug. 5, 2010

Related U.S. Application Data

(60) Provisional application No. 60/895,413, filed on Mar. 16, 2007.

(51) Int. Cl.
C12N 15/09 (2006.01)
C12N 15/29 (2006.01)
C12N 15/57 (2006.01)
C12N 9/50 (2006.01)
C07K 1/14 (2006.01)
C07K 1/22 (2006.01)

(52) U.S. Cl. ............. 435/69.1; 435/219; 435/252.3; 435/252.33; 435/320.1; 530/412; 530/413

(58) Field of Classification Search .................. None
See application file for complete search history.

(56) References Cited

U.S. PATENT DOCUMENTS

| | | | | |
|---|---|---|---|---|
| 5,663,304 A * | 9/1997 | Builder et al. | ............. | 530/399 |
| 5,766,897 A * | 6/1998 | Braxton | ............. | 435/463 |
| 5,811,098 A * | 9/1998 | Plowman et al. | ............. | 424/178.1 |
| 5,912,327 A * | 6/1999 | Li et al. | ............. | 530/412 |
| 6,165,746 A * | 12/2000 | Heitzmann et al. | ............. | 435/69.1 |
| 6,492,498 B1 * | 12/2002 | Vallera et al. | ............. | 530/391.7 |
| 6,593,106 B1 * | 7/2003 | Vicik | ............. | 435/69.1 |
| 6,610,479 B1 * | 8/2003 | Lundeberg et al. | ............. | 435/6 |
| 6,635,462 B1 * | 10/2003 | Ensor et al. | ............. | 435/195 |
| 6,642,036 B2 * | 11/2003 | Flint et al. | ............. | 435/135 |
| 6,645,739 B2 * | 11/2003 | Clark | ............. | 435/69.1 |
| 7,112,660 B1 * | 9/2006 | Domingues et al. | ............. | 530/351 |
| 7,202,216 B2 | 4/2007 | Sollid et al. | | |
| 7,265,093 B2 | 9/2007 | Khosla et al. | | |
| 7,303,871 B2 | 12/2007 | Hausch et al. | | |
| 7,320,788 B2 | 1/2008 | Shan et al. | | |
| 7,442,370 B2 * | 10/2008 | Sah et al. | ............. | 424/78.27 |
| 7,462,688 B2 | 12/2008 | Khosla et al. | | |
| 7,521,427 B2 * | 4/2009 | Powers et al. | ............. | 514/1.1 |
| 7,579,313 B2 | 8/2009 | Khosla et al. | | |
| 7,605,150 B2 | 10/2009 | Khosla et al. | | |
| 7,628,985 B2 | 12/2009 | Shan et al. | | |
| 7,651,848 B2 * | 1/2010 | Schlegl | ............. | 435/69.1 |
| 7,696,338 B2 * | 4/2010 | Neville, Jr. et al. | ............. | 536/23.4 |
| 7,776,545 B2 | 8/2010 | Khosla et al. | | |
| 2002/0018763 A1 * | 2/2002 | Zsebo et al. | ............. | 424/85.1 |
| 2004/0265298 A1 * | 12/2004 | Lin | ............. | 424/94.64 |
| 2005/0176932 A1 * | 8/2005 | Buus et al. | ............. | 530/350 |
| 2005/0227920 A1 * | 10/2005 | Lin | ............. | 514/12 |
| 2007/0082369 A1 * | 4/2007 | Best et al. | ............. | 435/7.2 |
| 2007/0099238 A1 * | 5/2007 | Sigalas et al. | ............. | 435/7.1 |
| 2007/0161572 A1 | 7/2007 | Sollid et al. | | |
| 2008/0044401 A1 | 2/2008 | Khosla et al. | | |
| 2008/0095710 A1 | 4/2008 | Shan et al. | | |
| 2008/0145356 A1 | 6/2008 | Hausch et al. | | |
| 2008/0213245 A1 | 9/2008 | Hausch et al. | | |
| 2008/0213427 A1 | 9/2008 | Hausch et al. | | |
| 2008/0213822 A1 | 9/2008 | Hausch et al. | | |
| 2008/0233102 A1 | 9/2008 | Khosla et al. | | |
| 2008/0299108 A1 | 12/2008 | Khosla et al. | | |
| 2008/0311161 A1 | 12/2008 | Gass | | |
| 2009/0042806 A1 | 2/2009 | Khosla et al. | | |
| 2009/0156490 A1 | 6/2009 | Khosla et al. | | |
| 2009/0280555 A1 | 11/2009 | Hausch et al. | | |
| 2009/0304754 A1 | 12/2009 | Robic | | |
| 2009/0312260 A1 | 12/2009 | Khosla et al. | | |
| 2009/0312272 A1 | 12/2009 | Khosla et al. | | |

FOREIGN PATENT DOCUMENTS

WO 2010/021752 2/2010
WO 2010/042203 4/2010

OTHER PUBLICATIONS

Rudolph, R., et al., 1996, "In vitro refolding of inclusion body proteins", The FASEB Journal, vol. 10, pp. 49-56.*
Bethune; et al., "Heterologous Expression, Purification, Refolding, and Structual-Functional Characterization of EP-B2, a Self-Activating Barley Cysteine Endprotease", Chemistry and Biology (2006), 13(6):637-47.
Gass; et al., "Effect of Barley Endoprotease EP-B2 on Gluten Digestion in the Intact Rat", The Journal of Pharmacology and Experimental Therapeutics (2006), 318(3):1178-86.

* cited by examiner

*Primary Examiner* — Manjunath Rao
*Assistant Examiner* — William W Moore
(74) *Attorney, Agent, or Firm* — Bozicevic, Field & Francis LLP; Pamela J. Sherwood

(57) ABSTRACT

Methods are provided for the production of gram to kilogram quantities of pro-EP-B2 (proenzyme form of EP-B2) in a lyophilized form. The methods include scalable fermentation, refolding and purification processes, which processes may be combined with lyophilization to yield a stable product.

25 Claims, 4 Drawing Sheets

SCALEABLE MANUFACTURING PROCESS FOR CYSTEINE ENDOPROTEASE B, ISOFORM 2

FEDERALLY SPONSORED RESEARCH AND DEVELOPMENT

This invention was made with Government support under contract DK063158 awarded by the National Institutes of Health. The Government has certain rights in this invention.

BACKGROUND OF THE INVENTION

In 1953, it was first recognized that ingestion of gluten, a common dietary protein present in wheat, barley and rye causes a disease, now called Celiac sprue, in sensitive individuals. Gluten is a complex mixture of glutamine- and proline-rich glutenin and prolamine molecules, which is thought to be responsible for disease induction. Ingestion of such proteins by sensitive individuals produces flattening of the normally luxurious, rug-like, epithelial lining of the small intestine known to be responsible for efficient and extensive terminal digestion of peptides and other nutrients. Clinical symptoms of Celiac sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations.

A related disease is dermatitis herpetiformis, which is a chronic skin eruption characterized by clusters of intensely pruritic vesicles, papules, and urticaria-like lesions. IgA deposits occur in almost all normal-appearing and perilesional skin of individuals with this disease. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Celiac sprue is generally considered to be an autoimmune disease, and the antibodies found in the serum of the patients support a theory of an immunological basis for the disease. Antibodies to tissue transglutaminase (tTG) and gliadin appear in almost 100% of the patients with active Celiac sprue, and the presence of such antibodies, particularly of the IgA class, has been used in diagnosis of the disease.

Gluten is so widely used, for example in commercial soups, sauces, ice creams, hot dogs, and other foods, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

One candidate for protease therapy is EP-B2 (Endoprotease B, Isoform 2), a papain-like cysteine protease that facilitates gluten breakdown and assimilation in germinating seeds of *Hordeum vulgare* (barley). In vitro and in vivo studies have shown that the zymogen (pro-EP-B2) form of this enzyme rapidly self-activates under gastric conditions, where mature EP-B2 can effectively detoxify gluten at pharmacologically reasonable doses (<5% w/w) (Bethune et al. (2006) Chem. Biol. 13(6):637-47; Gass et al. (2006) J Pharmacol Exp Ther. 318(3):1178-86). Controlled clinical studies to demonstrate the utility of this enzyme as supportive therapy for Celiac Sprue patients require relatively large amounts of enzyme, however, and there remains a need for methods to produce the enzyme in such amounts. The present invention meets this need.

SUMMARY OF THE INVENTION

Methods are provided for the production of large quantities of pro-EP-B2 (proenzyme form of EP-B2). The methods include scalable fermentation processes, refolding and purification processes, and lyophilization processes, all of which processes may be combined to yield a highly purified final product. The invention includes a fed-batch microbial fermentation system, in which the fermentation temperature and duration of protein expression are optimized to increase yield of the protein. In another aspect of the invention, a method is provided for refolding pro-EP-B2 using a fast dilution method, in which refolding can proceed at enzyme concentrations greater than 0.5 mg/ml. In another aspect, a lyophilization procedure is provided that provides product that allows stable storage of pro-EP-B2. The processes can be combined and are useful with fermentation volumes of industrial scale.

DETAILED DESCRIPTION OF THE EMBODIMENTS

Figure 1:
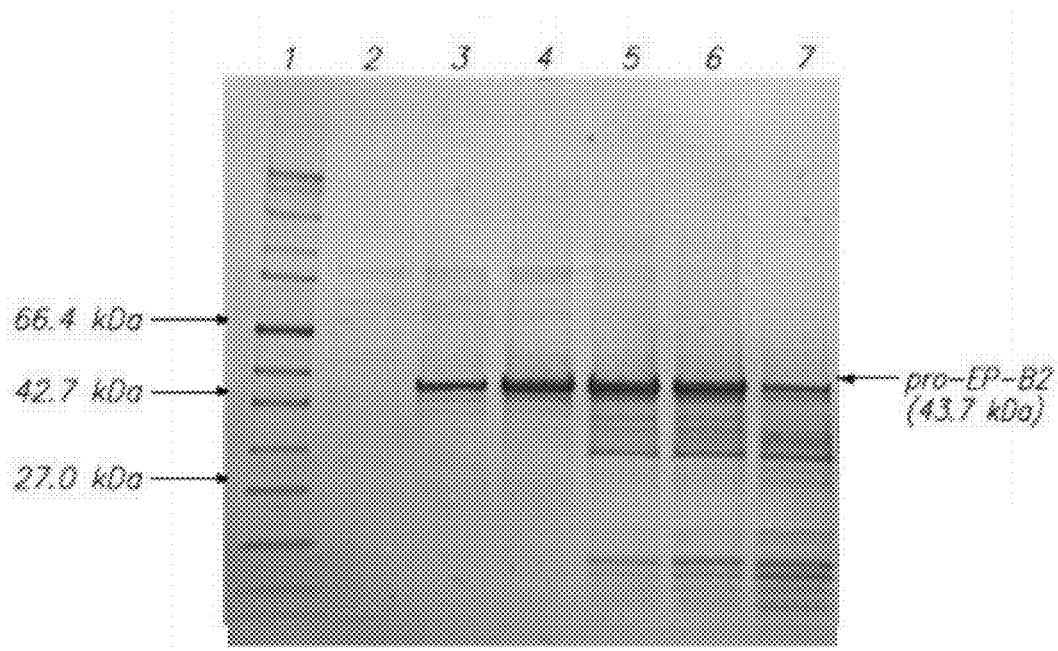
FIG. 1: Time-Dependent Degradation of pro-EP-B2. SDS-PAGE analysis of Ni-NTA affinity purified pro-EP-B2 from samples taken at various times relative to induction. Lanes: (1) protein marker, (2) −0.5 h, (3) +1 h, (4) +3 h, (5) +6 h, (6) +7 h, (7) +9 h. The negative time point is prior to induction and the positive time points are after induction.

Methods are provided for scalable production of recombinant pro-EP-B2 enzyme, where the enzyme is produced in an active proenzyme form. It will be understood by one of skill in the art by the term "active" that the proenzyme may not have the glutenase activity of the mature enzyme, but is competent to be activated by cleavage of the propeptide.

The methods of the invention allow the process yield to be maintained as the fermentation or reaction volume is scaled up. Purified, active enzyme is obtained from 1, 10, 50, 100 liter or greater fermentation quantities. This process comprises the steps of: producing the enzyme in a fermentation reaction with a microbial host, e.g. *E. coli*; extracting and solubilizing inclusion bodies containing pro-EP-B2; purifying the enzyme; and refolding of denatured enzyme.

As used herein, the term "small scale" refers to fermentation volumes of about, or less than about, 1 liter. The term "large scale" or "scaled up" is used herein to refer to fermentation volumes of greater than 1 liter, usually greater than about 10 liters, and which may be greater than about 100 liters, including but not limited to 200 liters, 500 liters, 1000 liters, and 10,000 liters, or more.

The methods of the present invention allow "scaled up" fermentation volumes, as described above, to maintain substantially consistent yields as compared to a small scale fermentation. Yield may be calculated by any convenient method, as long as it is consistently applied between the fermentation volumes, e.g. total protein synthesis/ml volume; desired protein synthesis/g. microbial cell mass; and the like. The yield in a scaled up fermentation volume, as compared to a comparable small scale fermentations (i.e. a fermentation comprises the same organisms, differing only in volume), is usually at least about 50%, more usually at least about 75%; and may be at least about 90% or greater.

ProEP-B2 is a proenzyme form of cysteine endoprotease B, isoform 2 (EP B2), which naturally occurs in *Hordeum vulgare* (barley). If the EP-B2 is delivered as a proenzyme, upon delivery into the acidic environment of the stomach, it rapidly self-activates into the mature enzyme (EP-B2), and efficiently proteolyses intact gluten proteins into oligopeptides. As used herein, the term "EP-B2" may refer to the mature form, the proenzyme form, or modified variants as described herein, unless otherwise specified. The use of EP-B2 provides advantages, including: (i) gluten can be fully detoxified before its arrival in an affected organ or before an autoimmune reaction is triggered by the gluten; (ii) the enzyme(s) do not require formulation via enteric coating; and (iii) enzyme stability in the presence of bile acids is not a major concern. As noted, if the EP-B2 is delivered as a proenzyme, upon delivery into the acidic environment of the stomach, it rapidly self-activates into the mature enzyme (EP-B2), and efficiently proteolyses intact gluten proteins into oligopeptides.

In some embodiments, the proEP-B2 is further engineered to delete the native signal sequence, which allows for high expression of proEP-B2 as inclusion bodies in *E. coli*. Optionally the sequence further comprises affinity tags to facilitate purification, e.g. N-terminal and/or C-terminal hexa-histidine tags, which have high affinity for commercially available nickel affinity resins. An example of a suitable proEP-B2 proenzyme sequence is provided in SEQ ID NO:1. An example of a suitable native proEP-B2 sequence is provided in SEQ ID NO:2. An example of a suitable mature enzyme form is provided in SEQ ID NO:3.

The specific activity of proEP-B2 is defined by the activity of the mature enzyme form, where 1 unit is defined as 1 μM p-nitroaniline released per minute from a chromogenic substrate CBz-Phe-Arg-pNA at room temperature. Enzyme formulations may be provided by the methods of the invention in which the specific activity is at least about 500 U/mg, at least about 1000 U/mg, or higher.

Typically, the compositions used in the practice of the invention will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In the methods of the invention, proEP-B2 is recombinantly produced by microbial fermentation, in a fermentation volume of from about 1 to about 10,000 liters, for example, a fermentation volume of about 10 to about 1000 liters. The fermentation may utilize any suitable microbial host cell and culture medium. *E. coli* is exemplary, but other microorganisms may be used, e.g. *S. cerevisiae, P. pastoris, Lactobacilli, Bacilli* and *Aspergilli*. Integrative or self-replicative vectors may be used for the purpose of introducing the proEP-B2 expression cassette into a host cell of choice.

In an expression cassette, the coding sequence for the proEP-B2 is operably linked to promoter, such as an inducible promoter. Inducible promoters are promoters that initiate increased levels of transcription from DNA under their control in response to some change in culture conditions, e.g., the presence or absence of a nutrient or a change in temperature.

A large number of promoters recognized by a variety of potential host cells are well known. These promoters can be operably linked to proEP-B2 polypeptide-encoding DNA by removing the promoter from the source DNA, if present, by restriction enzyme digestion and inserting the isolated promoter sequence into the vector. Promoters suitable for use with microbial hosts include the β-lactamase and lactose promoter systems (Chang et al., Nature, 275:617-624 [1978]; Goeddel et al., Nature, 281: 544 [1979]), alkaline phosphatase, a tryptophan (trp) promoter system (Goeddel, Nucleic Acids Res., 8: 4057 [1980]; EP 36,776), and hybrid promoters such as the tac promoter (deBoer et al., Proc. Natl. Acad. Sci. USA, 80: 21-25 [1983]). However, other known bacterial promoters are suitable. Their nucleotide sequences have been published, thereby enabling a skilled worker operably to ligate them to DNA encoding proEP-B2 polypeptide (Siebenlist et al., Cell, 20: 269 [1980]) using linkers or adaptors to supply any required restriction sites. Promoters for use in bacterial systems also will contain a Shine-Dalgarno (S.D.) sequence operably linked to the coding sequence. In some embodiments the inducible promoter is the lacZ promoter, which is induced with IPTG, as known in the art. Promoters and expression cassettes can also be synthesized de novo using well known techniques for synthesizing DNA sequences of interest.

The microbial host is grown to high density in a fermentation reactor, which will typically have controlled feeds for glucose. At an $OD_{600}$ of at least about 15, usually at least about 20, at least 25, at least about 30 or higher, expression of the recombinant protein is induced. In certain embodiments of the invention, production is maintained for around about 2 to around about 5 hours post induction, and may be from around about 2 to around about 3 hours post-induction. Longer periods of induction may be undesirable due to degradation of the recombinant protein. The temperature of the reaction mixture during induction is preferably from about 28° C. to about 32° C., usually from about 29° C. to about 31° C., and may be about 30° C.

The EP-B2 proenzyme is expressed as cytosolic inclusion bodies in microbial cells. To harvest inclusion bodies, a cell pellet is collected by centrifugation of the fermentation medium, frozen, thawed and resuspended in disruption buffer. The cells are lysed by conventional methods, e.g. sonication, homogenization, etc. The lysate is then resuspended in solubilization buffer, usually in the presence of urea at a concentration effective to solubilize proteins, e.g. from around about 5, 6, 7 M or greater. Resuspension may require mechanically breaking apart the pellet and stirring to achieve homogeneity.

The solubilized protein is purified. Purification methods may include affinity chromatography, reverse phase chromatography, gel exclusion chromatography, and the like. In some embodiments, affinity chromatography is used. For example, the protein may be provided with an epitope tag or his6 tag for convenient purification.

The purified protein is refolded by dilution into a buffer with a urea concentration of not more than about 0.8 M urea, usually not more than about 0.7 M urea, at a pH of from about 8 to about 11, usually at a temperature below about 10° C., usually below about 5° C. The protein concentration is preferably maintained at not more than about 1 mg/ml, usually not more than about 850 µg/ml. The refolding reaction is essentially complete by around about 24 hours, usually around about 15 to about 20 hours.

The refolded protein is polished. As used herein, the term "polishing" refers to the removal of trace impurities or closely related substances in final purification steps. Polishing methods may include, selective precipitation, reverse phase chromatography, gel exclusion chromatography, ion exchange chromatography, and the like. In some embodiments, anion exchange chromatography is used. For example, the specific activity of refolded protein is significantly improved after anion exchange polishing.

A lyophilized protein preparation is desirable for stability and ease of transport. Various such methods are known in the art. In one embodiment, the refolded protein is buffer exchanged into medium comprising from about 1 to about 5 mM, usually around about 2 mM 1-Thioglycerol; and from about 1 to about 10%, usually around about 5% saccharides, e.g. mannitol, sucrose, etc. The composition is then frozen and dried.

In one aspect, the present invention provides a purified preparation proEP-B2, which preparation may be provided as a bulk lyophilized powder; formulated into unit dosages; etc. The term "unit dosage form," refers to physically discrete units suitable as unitary dosages for human subjects, each unit containing a predetermined quantity of proEP-B2 in an amount calculated sufficient to produce the desired effect in association with a pharmaceutically acceptable diluent, carrier or vehicle. The specifications for the unit dosage forms of the present invention depend on the particular combination employed and the effect to be achieved, and the pharmacodynamics associated in the host.

In one aspect, the proEP-B2 is formulated into pharmaceutical compositions by combination with appropriate, pharmaceutically acceptable carriers or diluents, and is formulated into preparations in solid, semi-solid, liquid or gaseous forms, such as tablets, capsules, powders, granules, ointments, solutions, suppositories, injections, inhalants, gels, microspheres, and aerosols. As such, administration of the proEP-B2 and/or other compounds can be achieved in various ways, usually by oral administration. In pharmaceutical dosage forms, the proEP-B2 may be administered in the form of its pharmaceutically acceptable salts, or it may also be used alone or in appropriate association, as well as in combination with other pharmaceutically active compounds. The following methods and excipients are exemplary and are not to be construed as limiting the invention.

For oral preparations, the proEP-B2 can be used alone or in combination with another glutenase enzyme, such as a prolyl endopeptidase (PEP), including but not limited to *Sphingomonas capsulata* PEP and appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Although not required, oral formulations optionally comprise enteric coatings, so that the active agent is delivered to the intestinal tract. A number of methods are available in the art for the efficient delivery of enterically coated proteins into the small intestinal lumen. Most methods rely upon protein release as a result of the sudden rise of pH when food is released from the stomach into the duodenum, or upon the action of pancreatic proteases that are secreted into the duodenum when food enters the small intestine. For intestinal delivery, the enzyme is usually lyophilized in the presence of appropriate buffers (e.g. phosphate, histidine, imidazole) and excipients (e.g. cryoprotectants such as sucrose, lactose, trehalose). Lyophilized enzyme cakes are blended with excipients, then filled into capsules, which are enterically coated with a polymeric coating that protects the protein from the acidic environment of the stomach, as well as from the action of pepsin in the stomach. Alternatively, protein microparticles can also be coated with a protective layer. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate. Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) *J Control Release* 71(3):307-18.

Various methods for administration may be employed, but typically oral administration, for example with meals, is used to deliver the protease to the patient in need thereof. The dosage of the therapeutic formulation can vary widely, depending upon the nature of the disease, the frequency of administration, the manner of administration, the clearance of the agent from the host, and the like. The dose can be administered as needed; typically, the dose is administered daily, with meals, or as needed with meals to ensure that gluten consumed by the patient is detoxified. In one embodiment, the proEP-B2 is admixed with food, or used to pre-treat foodstuffs containing glutens. ProEP-B2 present in foods can be enzymatically active prior to or during ingestion, and may be encapsulated or otherwise treated to control the timing of activity.

The compositions of the invention can be used for prophylactic as well as therapeutic purposes. As used herein, the term "treating" refers both to the prevention of disease and the treatment of a disease or a pre-existing condition. The invention provides a significant advance in the treatment of ongoing disease, to stabilize or improve the clinical symptoms of the patient. Such treatment is desirably performed prior to loss of function in the affected tissues but can also help to restore lost function or prevent further loss of function. Evidence of therapeutic effect may be any diminution in the severity of disease, particularly as measured by the severity of symptoms such as fatigue, chronic diarrhea, malabsorption of nutrients, weight loss, abdominal distension, anemia, and other symptoms of Celiac Sprue. Other disease indicia include the presence of antibodies specific for glutens, the presence of antibodies specific for tissue transglutaminase, the presence of pro-inflammatory T cells and cytokines, damage to the villus structure of the small intestine as evidenced by histological or other examination, enhanced intestinal permeability, and the like.

Patients that may be treated with the compositions of the invention include those diagnosed with Celiac Sprue through one or more of serological tests, e.g. anti-gliadin antibodies, anti-transglutaminase antibodies, anti-endomysial antibodies; endoscopic evaluation, e.g. to identify celiac lesions; histological assessment of small intestinal mucosa, e.g. to detect villous atrophy, crypt hyperplasia, infiltration of intra-epithelial lymphocytes; and any GI symptoms dependent on inclusion of gluten in the diet. Amelioration of the above symptoms upon introduction of a strict gluten-free diet is a key hallmark of the disease. However, analysis of celiac patients has shown that a high level of patients believed to be in remission are, in fact, suffering malabsorption, as evidenced by indicia including, without limitation, xylose absorption tests, fecal fat analysis, lactulose/mannitol permeability tests, and the like. In some embodiments of the invention, patients are evaluated by examination of intestinal malabsorption for initial diagnosis, assessment, and/or monitoring during and after treatment.

Given the safety of oral proteases, they also find a prophylactic use in high-risk populations, such as Type I diabetics, family members of diagnosed celiac patients, HLA-DQ2 positive individuals, and/or patients with gluten-associated symptoms that have not yet undergone formal diagnosis. Such patients may be treated with regular-dose or low-dose (10-50% of the regular dose) enzyme. Similarly, temporary high-dose use of such an agent is also anticipated for patients recovering from gluten-mediated enteropathy in whom gut function has not yet returned to normal, for example as judged by fecal fat excretion assays.

Patients that can benefit from the present invention may be of any age and include adults and children. Children in particular benefit from prophylactic treatment, as prevention of early exposure to toxic gluten peptides can prevent initial development of the disease. Children suitable for prophylaxis can be identified by genetic testing for predisposition, e.g. by HLA typing; by family history, by T cell assay, or by other medical means. As is known in the art, dosages may be adjusted for pediatric use.

The therapeutic effect can be measured in terms of clinical outcome or can be determined by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Alternatively, one can look for a reduction in symptoms of the disease.

As used herein, compounds which are "commercially available" may be obtained from commercial sources including but not limited to Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

Compounds can also be made by methods known to one of ordinary skill in the art. As used herein, "methods known to one of ordinary skill in the art" may be identified though various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

The present invention relates generally to methods and reagents useful in treating foodstuffs containing gluten with enzymes that digest the proteins and oligopeptides toxic to Celiac sprue patients. Although specific enzymes are exemplified herein, any of a number of alternative enzymes and methods apparent to those of skill in the art upon contemplation of this disclosure are equally applicable and suitable for use in practicing the invention. The methods of the invention, as well as tests to determine their efficacy in a particular patient or application can be carried out in accordance with the teachings herein using procedures standard in the art. Thus, the practice of the present invention may employ conventional techniques of molecular biology (including recombinant techniques), microbiology, cell biology, biochemistry and immunology within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991); as well as updated or revised editions of all of the foregoing.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

This application specifically references U.S. Pat. Nos. 7,320,788; 7,303,871; 7,265,093 and 7,202,216, each of which is specifically incorporated by reference herein.

EXPERIMENTAL

Example 1

Materials and Methods

Physical Properties of pro-EP-82: The predicted molecular weight of recombinant pro-EP-B2 is 43.7 kDa. The protein has three disulfide bonds and an active site cysteine. The calculated pI of the protein is 6.4. The X-ray crystal structure of cysteine endoprotease EP-B2 bound to leupeptin has been solved to 2.2 Å (Protein Data Bank accession number 2FO5) and revealed the presence of three intramolecular disulfide bonds.

10 L Fed-Batch Fermentation: Recombinant pro-EP-B2 was produced as inclusion bodies in *E. coli* BL21(DE3)/pMTB1 cells using a 10 L fed-batch fermentation process. The general fermentation procedure used was as follows. A 250 ml inoculum was used that was grown overnight using a rotary shaker at 37° C. Fermentation temperature was maintained at 30° C. (or 37° C., in other fermentations). Starting at an $OD_{600}$ of 6-7, the fermentation was fed a sterile glucose feed solution at a constant rate of 3 ml/min. Protein expression was induced at an $OD_{600}$ of 13-15 using 800 μL of 1M IPTG. Unless otherwise specified, the fermentation was terminated between 2-4 h after induction. Fermentation broth samples (~50 ml) were taken at predetermined times before and after induction to evaluate degree and quality of pro-EP-B2 expression. Each sample was immediately flash frozen in an ethanol/dry ice bath and stored at −80° C. until further analysis. Prior to analysis, all samples were thawed at room temperature for 30-45 min followed by 37° C. for 10-15 min. Samples were then centrifuged at approximately 3200×g for 30 min at 4° C. The supernatant was discarded and the remaining pellet was washed with nominal amounts of water. Two grams of the resulting pellet were removed for further analysis. 25 ml of disruption buffer were added to each cell pellet mass, and sample tubes were vortexed to achieve homogeneity. The cell suspensions were lysed using sonication (Branson Sonifier 450® operated at setting 6, approximately 60 pulses). Subsequent inclusion body extraction/solubilization and purification steps were performed similarly to procedures described below. Solubilized or purified pro-EP-B2 samples were analyzed via SDS-PAGE.

Inclusion Body Isolation and Solubilization: The EP-B2 proenzyme was expressed as cytosolic inclusion bodies. All cell lysis, centrifugation, and stirring steps were performed at approximately 4° C. unless noted otherwise. At the end of each fermentation, the cell broth was centrifuged at 4400×g for 20 min, and, if necessary, the resulting cell pellet was stored at −80° C. To harvest inclusion bodies, the cell pellet was thawed at 37° C. and resuspended in disruption buffer (200 mM sodium phosphate buffer, pH 7.0, 200 mM NaCl, 2.5 mM DTT, 1.5 mM benzamidine, 2.5 mM EDTA, 2 μg/ml pepstatin A, 2 μg/ml leupeptin, 30% (v/v) glycerol). 1 μL of a 1:1 mixture of DNase I (10 U/μL) and RNase A (30 U/μL) was added for every 2 g (wet weight) of cell pellet. After stirring to achieve homogeneity, the cells were lysed using sonication (Branson Sonifier 450® operated at setting 6 for 1 min, put on ice for 5 min, cycle repeated 3-5 times, performed in 50-100 ml aliquots) or homogenization (Avestin C-3 Cell Homogenizer® operated at 15-20 kpsi, 3 passes, performed at room temperature). Generally, the lysed cell material was centrifuged at 45,000×g for 1 h. On occasions when such high centrifugal speeds were not attainable, the material was centrifuged at 10,000×g for 30-90 min. After discarding the supernatant, the pellet was washed with nominal amounts of water and then resuspended in solubilization buffer (50 mM Tris-Cl buffer, pH 8, 7M urea, 2 mM β-mercaptoethanol) to dissolve pro-EP-B2 inclusion bodies within the pellet. Satisfactory resuspension required mechanically breaking apart the pellet and stirring to achieve homogeneity. The solubilized material was centrifuged at 45,000×g for 1 h, and the supernatant was recovered for purification.

Protein Purification: His$_6$-tagged pro-EP-B2 was purified in its unfolded form by nickel affinity chromatography. Resin binding was performed in batch mode. The unfolded protein solution was stirred with Ni-NTA resin (Qiagen, Valencia, Calif.) for 2 h or more at 4° C. Approximately 0.7 ml of 50% Ni-NTA resin was used for every g of initial cell pellet. Wash and elution steps were performed either in batch or column systems. The protein-bound resin was washed twice with 10-fold excess solubilization buffer relative to the resin volume. The protein was eluted using three equal batches of elution buffer (50 mM Tris-Cl buffer, pH 8, 7M urea, 2 mM β-mercaptoethanol, 200 mM imidazole) with total eluate volume equal to 7.5 times the resin volume. The eluate was stored at 4° C. until the protein refolding step.

Protein Refolding: All protein refolding solutions were prepared at 4° C. unless otherwise noted. Protein refolding was performed via a batch dilution method. The eluate from Ni-NTA column purification was added to refolding buffer (100 mM Tris-Cl buffer, 5 mM EDTA, 2 mM β-mercaptoethanol, 15% (w/v) sucrose, pH 8) at 5 ml/min or faster while stirring the nascent refolding volume. At preparative scales between 0.1-10 g pro-EPB2, flow rates were adjusted such that unfolded protein was diluted into refolding buffer over the course of about 8 min. This fixed addition time gave similar refolding efficiency at different scales. A final protein concentration of 500-650 μg/ml and a final urea concentration of less than or equal to 0.7M were targeted for optimal folding. After the refolding solution was allowed to stir for 20-24 h, it was passed through a 0.2/0.45 μm filter to clarify the solution. The clarified pro-EP-B2 solution was then concentrated to the final desired concentration of 14-15 mg/ml using a tangential flow filtration system (Millipore Pellicon XL® with a 10 kDa cutoff membrane) or, alternatively, a centrifugal concentrator (Millipore Amicon Ultra-150-10, 000MWCO), depending upon volume handling requirements. If necessary, the final concentrated material was briefly centrifuged or passed through a 0.2 μm filter to remove residual aggregates. Refolded pro-EP-B2 solution was kept frozen at −20° C. or below or stored as lyophilized powder.

Concentration Dependence of pro-EP-B2 Refolding: To investigate the dependence of refolding efficiency on protein concentration, pro-EP-B2 refolding was evaluated at concentrations ranging from 100 to 850 μg/ml. For all concentrations, 5 ml of eluate at appropriate concentrations were added to 45 ml of refolding buffer (10× dilution) while stirring at 4° C. The 5 ml eluate volume was kept constant in all cases to remove buffer variability. After stirring for 21-22 h, the specific activity (U/mg) of the refolded product was measured. Each activity assay was performed in duplicate.

Refolding Kinetics: Pro-EP-B2 refolding kinetics were investigated at a refolding concentration of 660 μg/ml. To initiate refolding, 5 ml of eluate were added to 45 ml of refolding buffer at an approximate rate of 5 ml/min while stirring at 4° C. Over the course of approximately 50 h, 100 μL samples were withdrawn and tested for specific activity. Each activity assay was performed in duplicate. Data modeling was performed using Origin® software (Microcal Software Inc, Northampton, Mass.).

Redox State/pH Dependence of pro-EP-82 Refolding: The efficiency of pro-EP-B2 refolding was tested under different redox conditions. Redox states were controlled by using appropriate reduced/oxidized glutathione ratios (GSH: GSSG) in refolding buffer (100 mM Tris-Cl buffer, with 5 mM EDTA, 2 mM β-mercaptoethanol, 15% (w/v) sucrose, pH 8). The total glutathione concentration in the refolding volume was 5 mM. Four different redox conditions were tested: 1) 1:5 GSSG:GSH, 2) 1:5 GSH:GSSG, 3) 1:1 GSSG: GSH, 4) refolding buffer with no glutathione. Refolding efficiency as a function of pH was also evaluated using refolding buffer at pH 8.1 (control) and 8.8 (pH adjustments were performed at room temperature). Values lower than pH 8 were not investigated because of decreased solubility under these conditions. For all cases, refolding was performed by adding 5 ml of eluate to 45 ml of appropriately modified refolding buffer (10× dilution) while stirring at 4° C. The refolding concentration was approximately 450 μg/ml. Samples (200 μL) were taken periodically from the refolding volumes over the course of 21 h and tested for specific activity. Each activity assay was performed in duplicate.

SDS-PAGE Analysis of Refolded pro-EP-82 material: Pro-EP-B2 samples with varying specific activity (11 U/mg-1515 U/mg) were mixed to a final concentration of 1 mg/mL with SDS sample buffer with and without 5% β-mercaptoethanol. Each sample was denatured by boiling to 100° C. for 5 min. 5 μg of samples were loaded and separated electrophoretically by a 4-12% TRIS-CI SDS-PAGE gel (Bio-Rad, Hercules, Calif.).

HPLC Analysis of Refolded pro-EP-82 material: An Agilent 1100® HPLC system with a Shodex IEC QA-825 8u SAX anion exchange column was used. Samples of refolded pro-EP-B2 with varying specific activity (11 U/mg-1515 U/mg) were loaded onto the system through 50 [L injections of 1.5 mg/ml stock solutions. A two-buffer gradient (Buffer I/II) was employed where Buffer II was Buffer I (100 mM Tris-Cl buffer, 5 mM EDTA, 2 mM 1-Thioglycerol, pH 8.5)+ 1M NaCl. The gradient was run from 0-33% Buffer II. Protein was eluted as a sharp peak at a retention time of 5 min.

Protein polishing: 2 ml of approximately 15 mg/mL pro-EP-B2 solution in refolding buffer was diluted to 1.5 mg/ml in buffer A (100 mM Tris, pH 8.5, 5 mM EDTA and 2 mM 1-Thioglycerol. Resulting solution was loaded to a Q sepharose column (2.5 mL resin) in a gravity flow mode. After loading, the column was washed with 8 ml of buffer A. Bound pro-EP-B2 was eluted using a sodium chloride step gradient (0-400 mM sodium chloride in buffer A). Both load and elution fractions were analyzed by protein activity assay.

Lyophilization: Approximately 10 mg/ml pro-EP-B2 solutions in refolding buffer were buffer exchanged into lyophilization buffer (100 mM Tris-Cl buffer, 5 mM EDTA, 2 mM 1-Thioglycerol, and 4%/1% (w/v) mannitol/sucrose, pH 8.5). Increasing the pH of the lyophilization buffer to 8.5 (versus keeping it at pH 8, as for the refolding buffer) made it significantly easier to perform the buffer exchange step without loss of protein content. The buffer exchanged material was transferred in 0.5 ml aliquots to 3 ml glass vials. The vial openings were covered with parafilm that was punctured with small holes to allow for water removal. The solution was frozen by placing vials in a dry ice/ethanol slurry. The vials were then placed in a VirTis Freezemobile® 6xL lyophilizer operated with a condenser temperature of −80° C. and less than 100 mTorr for greater than 48 hours. The resulting powder was then stored at the desired temperature. To test activity, the powder was reconstituted in water at approximately pre-lyophilization concentrations.

Scale-Up of pro-EP-82 production: A 100 L fermentation process for the production of pro-EP-B2 was developed directly from the 10 L process. Due to the availability of more sophisticated instrumentation at the larger scale, the constant glucose feed was replaced by a variable feed that maintained a constant glucose concentration in the fermentation broth. Oxygen supplementation was also used to maintain a dissolved oxygen reading of 40%. These modifications allowed for induction to occur at an OD of 30 instead of 13-15. The induction period was maintained at 3 hours. The post-lysis centrifugation steps were replaced by a more scalable tangential flow filtration procedure. The cell lysate was first pumped through a GE Healthcare 10 kD hollow fiber cartridge (model #UFP-10-C-55), resulting in a three-fold volume reduction. The concentrated material was approximately diluted 1:1 with deionized water, and passed through the filter again until the pre-dilution volume was achieved. This dilution/concentration procedure was repeated once. A 1 μm filter was used to clarify the final concentrated material before continuing to the purification step. The cell lysis, purification, and refolding procedures were not modified significantly except for the use of appropriately scaled columns, vessels, filters and other required materials.

EP-82 Activity Assay: EP-B2 specific activity (U/mg of enzyme) was measured in a manner similar to that described earlier (Bethune et al. 2006, supra.) with the chromogenic reference substrate Z-Phe-Arg-pNA (Bachem, Torrance, Calif.). In brief, the assay protocol has two phases—self-activation of the proenzyme to mature EP-B2, followed by specific activity measurement of the mature enzyme. EP-B2 proenzyme samples were assayed for protein content (see Bradford Protein Assay, below) and then diluted into a volume of 50 μL refolding buffer to a concentration of 400 nM (proenzyme EP-B2 MW: 43.7 kDa). This volume was added to 100 μL of 500 mM acetate buffer (pH 4.5-4.6), and incubated at 30° C. to allow for enzyme activation (Bethune et al. 2006, supra). After exactly 30 min, the entire volume was added to a cuvette containing 8504 substrate solution in 5% (v/v) DMSO/H$_2$O (50 μM substrate concentration in final assay volume). The reaction was immediately followed by monitoring A$_{410}$ at room temperature with a UV/Vis is spectrophotometer (Lambda 35, Perkin-Elmer, 4-nm slit width). The reaction rate was measured from the initial slope of the A$_{410}$ vs time, and converted to activity units using $\epsilon_{410}$=8800 M$_{-1}$ cm$_{-1}$ for pNA. 1 Unit is defined as 1 μM pNA released per min.

Bradford Protein Assay: All protein concentrations were measured using a Bradford protein assay (Bio-Rad, USA), which also correlated well with A$_{280}$ measurements. Bradford reaction mixtures were incubated for 10 min before measuring A$_{595}$ (Spectronic 20 Genesys® spectrophotometer, 8 nm slit width). Bovine serum albumin (New England Biolabs, Ipswich, Mass.) was used to create the calibration curve.

Results

10 L Fed Batch Fermentation and Purification of Pro-EP-B2: The proenzyme form of EP-B2 was initially produced via a 10 L fed-batch fermentation. During development of this process, it was observed that pro-EP-B2 undergoes time-dependent degradation upon induction of protein expression. In an SDS-PAGE gel of Ni-NTA purified samples taken at various times relative to induction, a single, strong band is seen at the molecular weight of pro-EP-B2 (43.7 kDa) at 3 h after induction. However, by 6 h, a heterogeneous mixture of low molecular weight bands is visible and by 9 h, the major pro-EP-B2 band is significantly reduced while the low molecular weight bands have become more prominent. Similar results were seen in a 37° C. fermentation time-course, but with more rapid degradation.

Through further analysis of the 30° C. fermentation, an optimal protein expression window between 2.6-4.7 h post-induction was determined, during which pro-EP-B2 could be recovered with significant yield and minimal degradation. The proenzyme generally expresses as a doublet or triplet under these conditions. Because all forms of pro-EP-B2 activate into the identical mature EP-B2 protein, we conclude that the pro-proteins differ only at the N-terminus.

It was also observed that purified pro-EP-B2 yields increase by only 11% between the 2.6 h and 4.7 h protein expression periods. Thus, it appears that the bulk of the protein production occurred within the first three hours after induction. Typically the yield from larger-scale pro-EP-B2 extraction and purification (~100 g of cell pellet) ranged from approximately 0.25-0.3 g of purified pro-EP-B2 per L of fermentation culture, with higher yields corresponding to longer protein expression periods within the defined timeframe. The purity of nickel-affinity purified material was estimated to be 80-95% pro-EP-B2 based on SDS-PAGE analysis.

Concentration Dependence of pro-EP-82 Refolding: Protein refolding is a key step in the overall development of a scalable production process for pro-EP-B2. Both dialysis and column-based refolding methods were initially evaluated. In the column-refolding method, the purification and refolding steps were combined. Pro-EP-B2 from the solubilized fraction of the lysate was bound to Ni-NTA resin. After sufficient washing, the resin-bound pro-EP-B2 was incubated in refolding buffer overnight at 4° C. This method was unsuccessful, because only a small fraction of the pro-EP-B2 (approximately <30%) could be eluted under non-denaturing conditions. A fast dilution method, in which the denatured polypeptide is rapidly added to refolding buffer under constantly stirred conditions, proved to be a simple and reliable process. Early dilution studies targeted refolding concentrations around 100 μg/ml, but the volume requirements associated with this specification were deemed impractical at larger scales. Thus, refolding at higher concentrations was investigated. FIG. 1 shows specific activity versus refolding concentration. The data suggests that the dilution method yields comparable refolding efficiencies in a concentration range of 100-850 μg/ml. Therefore high concentration refolding (>500 μg/ml) was implemented in pro-EP-B2 preparations.

Figure 2:
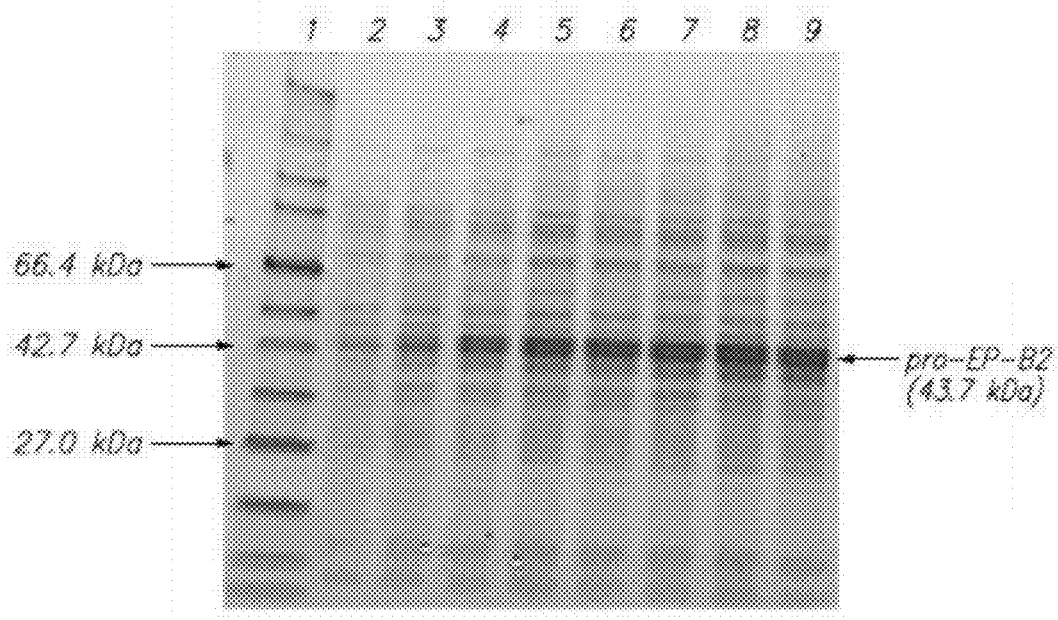
FIG. 2: Optimal Expression Window for pro-EP-B2 in 30° C. Fermentation. SDS-PAGE analysis of solubilized pro-EP-B2 inclusion bodies from samples taken at various times relative to induction. Lanes: (1) protein marker, (2) −0.2 h, (3) +0.4 h, (4) +0.9 h, (5) +1.3 h, (6) +1.6 h, (7) +2.6 h, (8) +3.6 h, (9) +4.7 h. The negative time point is prior to induction, and the positive time points are after induction.

Pro-EP-B2 Refolding Kinetics: To investigate the kinetics of pro-EP-B2 refolding at higher protein concentrations, the specific activity of pro-EP-B2, refolded at a concentration of 650 μg/ml, was monitored as a function of time. As shown in FIG. 2, the specific activity plateaus at 1000 U/mg by 15-20 hrs. The data was fit to a first order folding rate equation (k=0.15 hr$_{-1}$, R$_2$=0.887), consistent with the hypothesis that refolding is a unimolecular process (Middelberg 2002).

Figure 3:
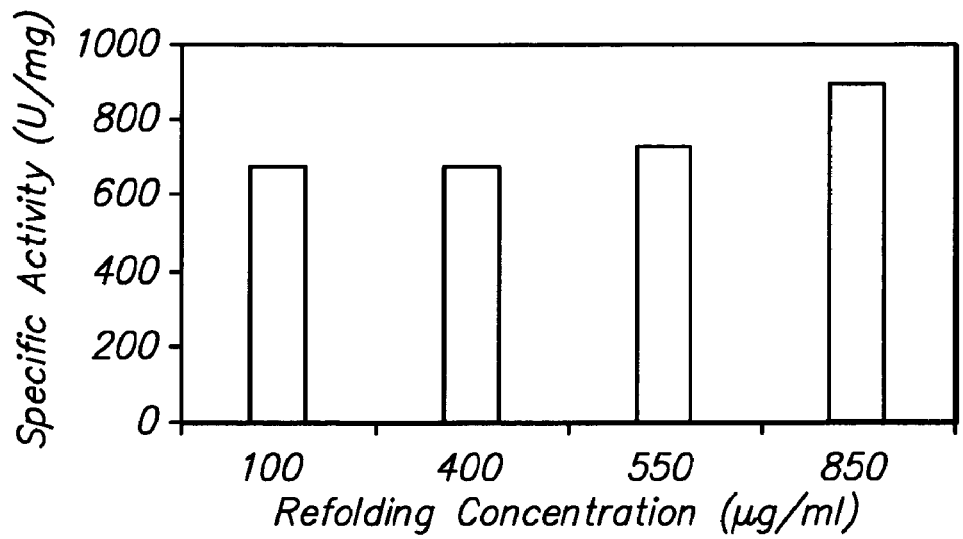
FIG. 3: Effect of Protein Concentration on Refolding Efficiency. Specific activity of refolded pro-EP-B2 was measured approximately 21 h after addition of unfolded protein to the refolding volume at concentrations ranging from 100 to 850 μg/μl.

Redox/pH Dependence of pro-EP-82 Refolding: Because EP-B2 has three conserved disulfide bonds, the importance of the redox environment on protein refolding was studied. Different ratios of reduced and oxidized glutathione were used to control the redox state. FIG. 8 shows data on the refolding efficiencies in these environments. It appears that the redox environment does not have a strong impact on either the kinetics or final refolding efficiencies. Because the pH of the refolding solution influences the propensity with which disulfide bonds can form, the dependence of refolding on pH was also investigated. The data in FIG. 3 shows that increasing the pH of the refolding buffer from 8.1 to 8.8 has no clear effect on refolding efficiency. Lower pH values were not evaluated, because protein solubility drops sharply below pH 8, presumably due to its isoelectric point (calculated pI is 6.4).

Heterogeneity of Refolding Step: Samples of refolded pro-EP-B2 of varying specific activity (11-1515 U/mg) were examined using SDS-PAGE under both non-reducing and reducing conditions. (FIG. 4a) In addition to a monomeric pro-EP-B2 band, putatively cross-linked or aggregated forms of pro-EP-B2 were visible under non-reducing conditions as high molecular weight bands. These bands collapsed to the monomeric pro-EP-B2 band under reducing conditions. For any given sample, the ratio of monomeric pro-EP-B2 under reducing versus non-reducing conditions appeared to correlate with its specific activity, suggesting that the aggregated protein had low or no activity. Thus, the unreduced:reduced ratio of monomeric protein was least for pro-EPB2 from samples B (lanes 4-5) and D (lanes 8-9) which had the lowest specific activities (305 and 11 U/mg respectively). The ratio was highest for sample F (lanes 12-13), which had the highest specific activity (1515 U/mg).

Figure 4:
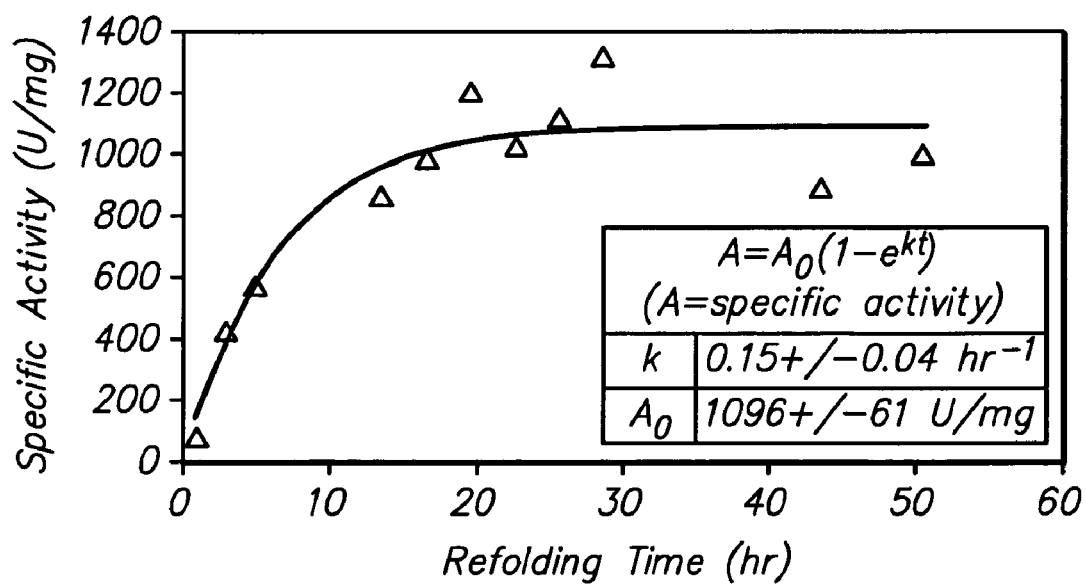
FIG. 4: Kinetics of Refolding. Specific activity of pro-EP-B2 refolded at 660 μg/ml was measured over the course of approximately 50 h. Data was fit to a first order reaction equation using Microcal Origin Software v. 6.0
Figure 5:
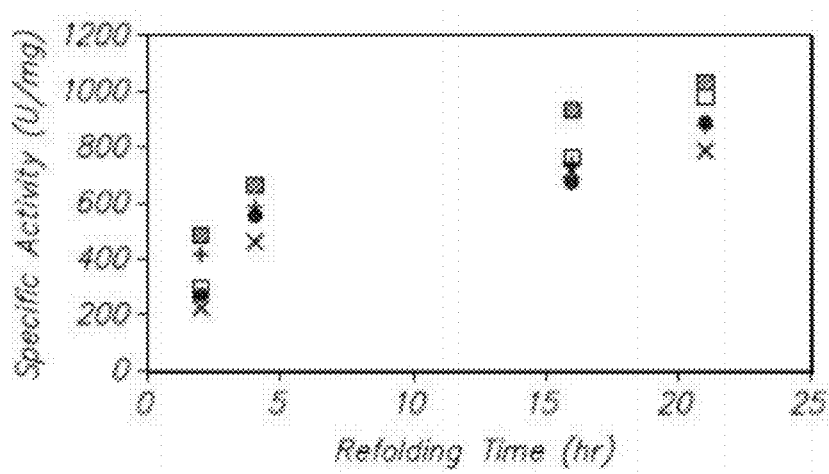
FIG. 5: Effect of Redox Environment and pH on Protein Refolding. Specific activity of pro-EP-B2 was measured over the course of 21 h under different redox and pH conditions. The following conditions were evaluated: 1) 1:5 GSSG:GSH (+), 2) 1:5 GSH:GSSG (X), 3) 1:1 GSSG:GSH (□), 4) refolding buffer, pH 8.1/no glutathione (■), 5) refolding buffer, pH 8.8/no glutathione (●).
Figure 6A:
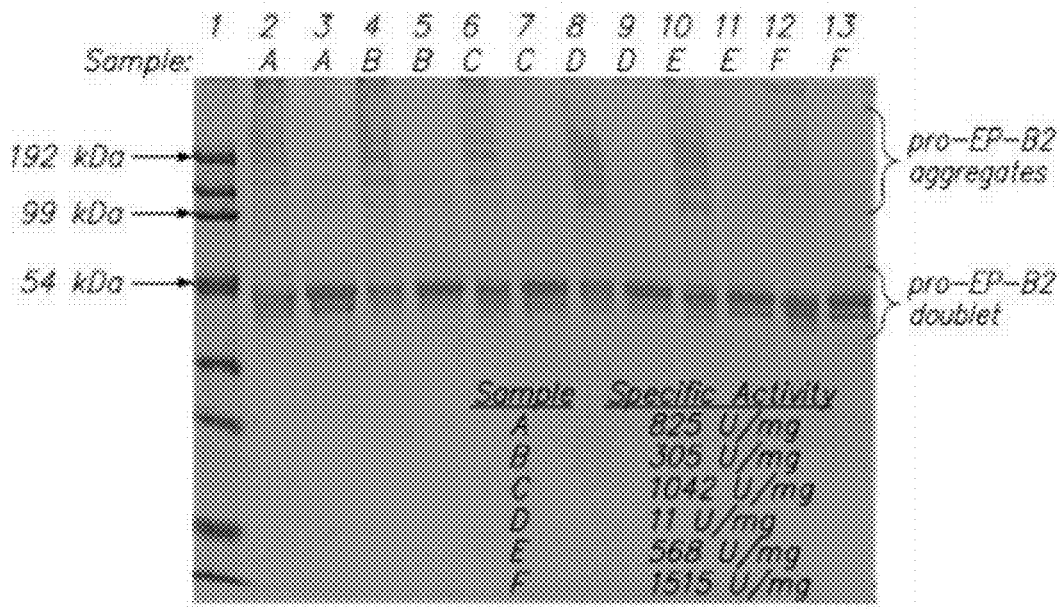
FIG. 6a: SDS-PAGE Analysis of Refolded pro-EP-B2 Samples. Pro-EP-B2 samples with varying specific activity were analyzed via SDS-PAGE under non-reducing and reducing conditions. For each sample, two lanes are shown, with the first lane containing protein denatured under non-reducing conditions and the second lane containing protein denatured under reducing conditions. Lanes: (1) Protein Marker, (2)-(3) Sample A, (4)-(5) Sample B, (6)-(7) Sample C, (8)-(9) Sample D, (10)-(11) Sample E and (12)-(13) Sample F.
Figure 6B:
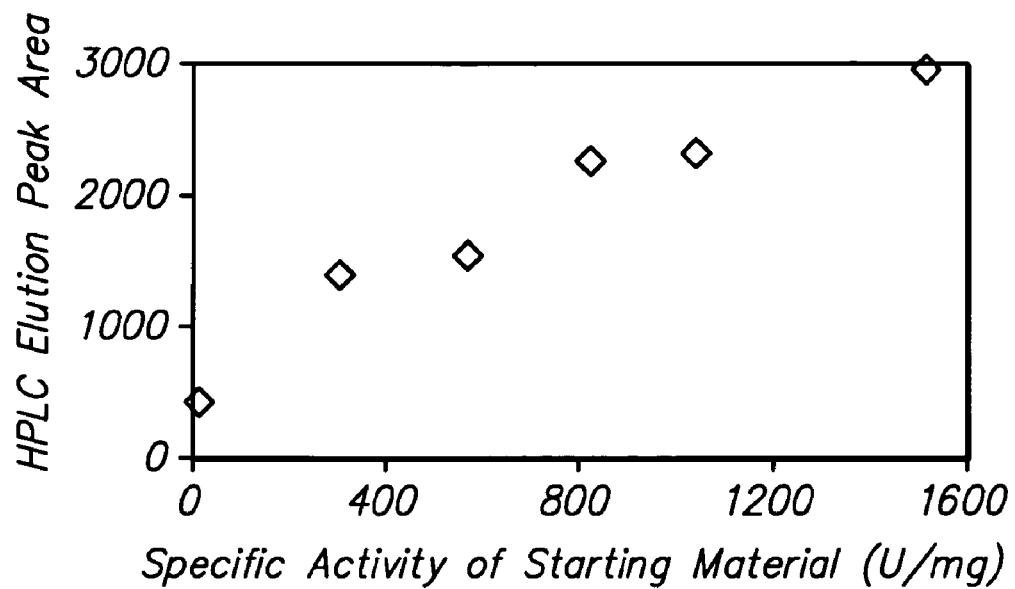
FIG. 6b: HPLC anion-exchange purification of refolded pro-EP-B2 samples. Refolded pro-EP-B2 samples of varying specific activity were analyzed via anion exchange HPLC. The area of the elution peak is plotted against the specific activity of the original sample.
Figure 7:
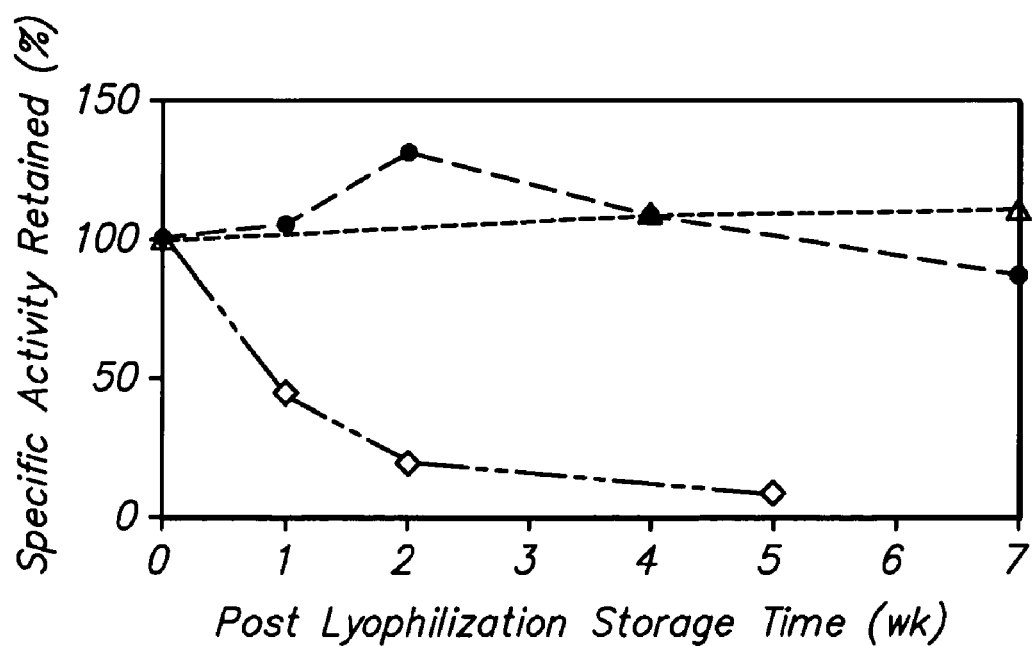
FIG. 7: Stability of Lyophilized versus Liquid pro-EP-B2 Preparations. Specific activity was measured of reconstituted pro-EP-B2 lyophilized powder stored at 4° C. (▲) and room temperature (●) as well as pro-EP-B2 liquid solution (♦) stored 4° C. over a seven week period to assess enzyme stability.

A more quantitative assay for correlating monomer content to specific activity was developed using anion-exchange HPLC. Under the chromatographic conditions described in the Materials and Methods section, a single sharp peak containing highly enriched monomeric pro-EP-B2 was observed. Analysis of the pro-EP-B2 samples shown in FIG. 4A revealed a strong correlation between peak area and the specific activity of the starting material (FIG. 4B). SDS-PAGE analysis of the eluate from the preparative anion exchange chromatography column showed >90% monomeric pro-EP-B2 in the form of three major bands of very similar molecular weight. These bands were identified as pro-EP-B2 by tryptic digestion followed by LC-MS analysis.

Concentration of Refolded pro-EP-82: A final pro-EP-B2 concentration of 12-15 mg/ml was targeted to facilitate preparation of dosage units containing 50-200 mg protein. To achieve this goal, the folded protein was clarified and concentrated. The clarification step eliminated any residual turbidity from the refolding volume. Removal of this turbidity, a likely product of aggregation, was essential to achieve desirably high concentrations. Furthermore, the yield data for a typical 200 mg preparation (Table I) shows that this clarification step was performed without appreciable protein or activity loss.

TABLE I

Process Yields. Stepwise bulk protein recovery and specific activity for preparations of concentrated, refolded pro-EP-B2 at various scales.

| | 0.2 g of pro-EP-B2 | | 15 g of pro-EP-B2 | | 42 g of pro-EP-B2 | |
|---|---|---|---|---|---|---|
| | Specific Activity (U/mg) | Bulk Protein (% Retained) | Specific Activity (U/mg) | Bulk Protein (% Retained) | Specific Activity (U/mg) | Bulk Protein (% Retained) |
| Post Purification | N/A | 100 | N/A | 100 | N/A | 100 |
| Post Refolding | 1150 | 75 | 1150 | — | — | — |
| Post Clarification | 1050 | 85 | 1500 | — | 1200 | 90 |
| Post Concentration | 1300 | 65 | 1000 | 65 | 1600 | 55 |

Polishing: A simple anion exchange chromatography was developed that improved the specific activity of the refolded protein by at least 2 fold by removing misfolded or aggregated protein during refolding (table below).

| Anion Exchange load activity (U/mg) | Anion Exchange Eluate Average Activity (U/mg) |
|---|---|
| 731 | 6637 |

Lyophilization: A simple lyophilization procedure was developed that yielded pro-EP-B2 powder with 85% restorable activity after storage at room temperature. FIG. 10 shows activity as a function of storage time. Over the course of a number of weeks, the specific activities of resuspended powders stored at both 4° C. and room temperature were stable. In contrast, a pro-EP-B2 preparation stored in solution form at 4° C. underwent a significant activity loss by five weeks of storage.

Scaled-Up Production of pro-EP-B2: To provide sufficient amounts of EP-B2 for initial toxicology and clinical studies, the pro-EP-B2 production process was scaled to produce 10-100 grams of concentrated, refolded pro-EP-B2 per batch. To this end, a 100 L fermentation process was developed that yielded approximately 0.5 g purified pro-EP-B2 per L of fermentation culture. At the 100 L scale, the post-lysis centrifugation steps were replaced by a more scaleable tangential flow filtration procedure. Based on protein concentration measurements and SDS-PAGE analysis, an estimated 60-80% of the pro-EP-B2 in the lysed material was recovered. Table I summarizes the recovery and specific activity of a 15 g and a 42 g preparation of pro-EP-B2. Overall, the data is comparable to that observed for the small-scale (200 mg) preparations, demonstrating that the process is scalable.

The development of an efficient, scalable pro-EP-B2 production process facilitates the production of gram to kilogram quantities of pro-EP-B2 for non-clinical safety and clinical studies as well as eventual commercialization. Achieving this goal entailed four critical steps: 1) pro-EP-B2 synthesis using an E. coli high-density fermentation system, 2) extraction and solubilization of inclusion bodies containing pro-EP-B2, 3) affinity-based purification, and 4) refolding of denatured pro-EP-B2. It was observed that over-expression of recombinant pro-EP-B2 resulted in significant proteolysis of the enzyme by the host cell. A solution to the degradation issue was found by identifying an expression window during which pro-EP-B2 could be made with negligible degradation products and high yields of 0.25-0.3 g of purified protein/L of culture at the 10 L scale.

It was anticipated that productivity and product quality would be critically influenced by the refolding step. Early work had shown that refolding could be simply achieved via a fast dilution method. Refolding concentrations in this system were controlled at 100 μg/ml or less. However, refolding at such low concentrations is impractical at larger scales. With the present methods, refolding at concentrations up to 850 μg/ml with resulting specific activities comparable to those seen at 100 μg/ml is possible, and the refolding concentration can be increased even further. An important nuance to the refolding step centers on the urea concentration in the refolding volume. In all the refolding experiments, the urea concentration was maintained at 0.7 M or lower. Early studies had suggested that a urea concentration above 1 M significantly reduced refolding efficiency. Reduction of denaturant is more important than refolding concentration over a concentration range of practical interest. A study of pro-EP-B2 refolding kinetics showed that the refolding process was unimolecular and essentially complete by about 15-20 h. Using a more alkaline refolding buffer did not result in faster refolding of pro-EP-B2, suggesting that the thiolate concentration at pH 8 is adequately high.

The impact of redox parameters on refolding yield was also evaluated. The redox environment was adjusted by modifying the refolding buffer with various ratios of reduced and oxidized glutathione at a total concentration of 5 mM. There was no significant difference between the conditions tested, both with respect to effect on refolding kinetics and the final specific activity of the refolded protein. This was surprising, because pro-EP-B2 has three conserved disulfide bonds. The redox environment is not a limiting parameter in the pro-EP-B2 refolding process; disulfide bond formation is likely achieved by air oxidation and bond shuffling is enabled by the low concentrations of β-mercaptoethanol (2 mM). The heterogeneity of the refolding process was observed through comparative SDS-PAGE analysis under reducing versus non-reducing conditions. A mixture of monomeric and oligomeric forms of the protein was observed under non-reducing conditions. Although the precise inter-polypeptide crosslinking sites were not identified, the heterogeneity highlighted the potential for further improving the efficiency of the refolding process. To quantify the fraction of monomer in individual enzyme preparations, an anion-exchange HPLC method was developed for separation of this species from oligomers as well as residual misfolded polypeptides. This method showed a strong correlation between monomeric content and specific activity, suggesting that most of the enzyme activity could be assigned to the monomeric form of EP-B2. Importantly, this finding shows that an anion-exchange polishing step can produce pro-EP-B2 with higher and more reproducible specific activity.

A simple lyophilization process was developed that yielded >85% restorable activity after seven weeks of storage at room temperature. The stability of lyophilized proteins is highly dependent on aggregation, which can occur at any stage of the process for both physical and chemical reasons. For example, removal of the hydration shell of a protein during the drying process may induce denaturation and aggregation. Reactions involving protein thiols, such as oxidation and β-elimination may also induce instability. An increase in oxygen concentration during the freezing process may also accelerate undesirable oxidation. This is especially important for pro-EP-B2, which has an active site cysteine.

The pro-EP-B2 process was successfully scaled from 10 L to 100 L with reproducible yields. Due to the availability of additional equipment at the larger scale, the fermentation process generated 0.5 g of purified protein/L of culture (compared to 0.25-0.3 g/L at the 10 L scale). A constant glucose feed used at the 10 L scale was replaced by a variable feed that maintained a constant glucose concentration in the fermentation broth. Oxygen supplementation was also used to maintain a dissolved oxygen reading of 40%. These modifications allowed for induction to occur at an OD of 30 instead of 13-15, which improved pro-EP-B2 yield accordingly. Also, at the 100 L scale, inclusion body harvesting was performed via a simple tangential flow filtration procedure as compared to high-speed centrifugation. A key challenge was the development of a scalable refolding process. The simplicity of the dilution method made it an attractive option during scale-up. In terms of capital investment, only a cooled stir tank and feed pump were required to reconstitute enzymatic activity. Together, these results provide a way for the manufacture of the zymogen form of cysteine endoprotease EP-B2 in quantity and quality suitable for preclinical and clinical development.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Any methods, devices and materials similar or equivalent to those described herein can be used in the practice or testing of the invention.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method for producing a self-activating *Hordeum vulgare* cysteine endoprotease B, isoform 2 proenzyme (proEP-B2), the method comprising:
producing proEP-B2 in a fermentation reaction with a microbial host;
extracting inclusion bodies containing proEP-B2 from said microbial host,
solubilizing the inclusion bodies in 5 M or greater urea to produce solubilized, denatured proEP-B2;
purifying said solubilized, denatured, proEP-B2; and
refolding said purified, solubilized, denatured pro-EP-B2 by rapid dilution into buffer comprising not more than 0.7 M urea under constant stirring wherein the protein concentration during refolding is maintained at greater than 500 µg/ml to provide a proEP-B2 enzyme composition capable of self-activation at acidic pH.

2. The method of claim 1, wherein the fermentation reaction is in a volume greater than 10 liters.

3. The method of claim 1, wherein the fermentation reaction is in a volume greater than 100 liters.

4. The method of claim 2, wherein the microbial host comprises polynucleotide sequences encoding proEP-B2, in the absence of the native signal sequence, operably linked to an inducible promoter.

5. The method of claim 4, wherein the microbial host is *E. coli*.

6. The method of claim 5, wherein the proEB-B2 enzyme is harvested after inducing transcription from said promoter for 2 to 5 hours, at a temperature of from 28° C. to about 32° C.

7. The method of claim 6, wherein the proEB-B2 enzyme is harvested after inducing transcription from said promoter for about 3 hours.

8. The method of claim 4, wherein the polynucleotide sequences encoding proEP-B2 comprise at least one affinity tag to facilitate purification.

9. The method of claim 8, wherein the affinity tag is a terminal hexa-histidine sequence.

10. The method of claim 9, wherein the proEP-B2 enzyme is purified by nickel affinity chromatography.

11. The method of claim 1, wherein the proEP-B2 enzyme concentration during refolding is maintained at less than 1 mg/ml.

12. The method of claim 11, further comprising purification of the proEP-B2 enzyme by a combination of two or more steps of selective precipitation, reverse phase chromatography, gel exclusion chromatography, and ion exchange chromatography.

13. The method of claim 11, further comprising lyophilizing the proEP-B2 enzyme composition.

14. The method of claim 11, wherein the proEP-B2 enzyme composition has a specific activity of at least about 500 U/mg when activated at acidic pH, where 1 unit is defined as 1 µM p-nitroaniline released per minute from a chromogenic substrate CBz-Phe-Arg-pNA at room temperature.

15. The method of claim 14, wherein the proEP-B2 enzyme composition has a specific activity of at least 1000 U/mg when activated at acidic pH.

16. A method of producing a self-activating active cysteine endoprotease B, isoform 2 proenzyme (proEP-B2) from cytosolic inclusion bodies, the method comprising:
solubilizing the cytoplasmic inclusion bodies by mechanical dissociation in urea at a concentration of at least 7M to produce solubilized, denatured, proEP-B2, purifying said solubilized, denatured, proEP-B2; and
refolding said purified, solubilized, proEP-B2, by rapidly diluting the solubilized proEP-B2 into buffer comprising not more than 0.7 M urea, wherein the protein concentration is maintained at 500 μg/ml concentration and less than 1 mg/ml to provide a proEP-B2 enzyme composition capable of self-activation at acidic pH.

17. The method of claim 16, wherein the cytoplasmic inclusion bodies are produced in a fermentation reaction with a microbial host comprising polynucleotide sequences encoding proEP-B2, in the absence of the native signal sequence, operably linked to an inducible promoter.

18. The method of claim 17, wherein the microbial host is *E. coli*.

19. The method of claim 17, wherein the polynucleotide sequences encoding proEP-B2 comprise at least one affinity tag to facilitate purification.

20. The method of claim 19, wherein the affinity tag is a terminal hexa-histidine sequence.

21. The method of claim 20, wherein the proEP-B2 enzyme is purified by nickel affinity chromatography.

22. The method of claim 16, further comprising purification of the proEP-B2 enzyme by a combination of two or more steps of selective precipitation, reverse phase chromatography, gel exclusion chromatography, and ion exchange chromatography.

23. The method of claim 16, further comprising lyophilizing the proEP-B2 enzyme composition.

24. The method of claim 16, wherein the refolded proEP-B2 enzyme is formulated in a composition that when activated at acidic pH has a specific activity of at least 500 U/mg, where 1 unit is defined as 1 μM p-nitroaniline released per minute from a chromogenic substrate CBz-Phe-Arg-pNA at room temperature.

25. The method of claim 24, wherein the proEP-B2 enzyme composition has a specific activity of at least 1000 U/mg when activated at acidic pH.

* * * * *

```
                        SEQUENCE LISTING

<160> NUMBER OF SEQ ID NOS: 3

<210> SEQ ID NO 1
<211> LENGTH: 401
<212> TYPE: PRT
<213> ORGANISM: Hordeum vulgare

<400> SEQUENCE: 1

Met Gly Ser Ser His His His His His Ser Ser Gly Leu Val Pro
1               5                   10                  15

Arg Gly Ser His Met Ala Ser Met Thr Gly Gly Asn Asn Met Gly Arg
            20                  25                  30

Asp Pro Cys Ser Ala Ile Pro Met Glu Asp Lys Asp Leu Glu Ser Glu
        35                  40                  45

Glu Ala Leu Trp Asp Leu Tyr Glu Arg Trp Gln Ser Ala His Arg Val
    50                  55                  60
```

-continued

Arg Arg His His Ala Glu Lys His Arg Phe Gly Thr Phe Lys Ser
65                  70                  75                  80

Asn Ala His Phe Ile His Ser His Asn Lys Arg Gly Asp His Pro Tyr
                85                  90                  95

Arg Leu His Leu Asn Arg Phe Gly Asp Met Asp Gln Ala Glu Phe Arg
            100                 105                 110

Ala Thr Phe Val Gly Asp Leu Arg Arg Asp Thr Pro Ser Lys Pro Pro
        115                 120                 125

Ser Val Pro Gly Phe Met Tyr Ala Ala Leu Asn Val Ser Asp Leu Pro
    130                 135                 140

Pro Ser Val Asp Trp Arg Gln Lys Gly Ala Val Thr Gly Val Lys Asp
145                 150                 155                 160

Gln Gly Lys Cys Gly Ser Cys Trp Ala Phe Ser Thr Val Val Ser Val
                165                 170                 175

Glu Gly Ile Asn Ala Ile Arg Thr Gly Ser Leu Val Ser Leu Ser Glu
            180                 185                 190

Gln Glu Leu Ile Asp Cys Asp Thr Ala Asp Asn Asp Gly Cys Gln Gly
        195                 200                 205

Gly Leu Met Asp Asn Ala Phe Glu Tyr Ile Lys Asn Asn Gly Gly Leu
    210                 215                 220

Ile Thr Glu Ala Ala Tyr Pro Tyr Arg Ala Ala Arg Gly Thr Cys Asn
225                 230                 235                 240

Val Ala Arg Ala Ala Gln Asn Ser Pro Val Val His Ile Asp Gly
                245                 250                 255

His Gln Asp Val Pro Ala Asn Ser Glu Glu Asp Leu Ala Arg Ala Val
            260                 265                 270

Ala Asn Gln Pro Val Ser Val Ala Val Glu Ala Ser Gly Lys Ala Phe
        275                 280                 285

Met Phe Tyr Ser Glu Gly Val Phe Thr Gly Glu Cys Gly Thr Glu Leu
    290                 295                 300

Asp His Gly Val Ala Val Val Gly Tyr Gly Val Ala Glu Asp Gly Lys
305                 310                 315                 320

Ala Tyr Trp Thr Val Lys Asn Ser Trp Gly Pro Ser Trp Gly Glu Gln
                325                 330                 335

Gly Tyr Ile Arg Val Glu Lys Asp Ser Gly Ala Ser Gly Gly Leu Cys
            340                 345                 350

Gly Ile Ala Met Glu Ala Ser Tyr Pro Val Lys Thr Tyr Ser Lys Pro
        355                 360                 365

Lys Pro Thr Pro Arg Arg Ala Leu Gly Ala Arg Glu Ser Leu Asn Ser
    370                 375                 380

Ser Ser Val Asp Lys Leu Ala Ala Ala Leu Glu His His His His His
385                 390                 395                 400

His

<210> SEQ ID NO 2
<211> LENGTH: 348
<212> TYPE: PRT
<213> ORGANISM: Hordeum vulgare

<400> SEQUENCE: 2

Cys Ser Ala Ile Pro Met Glu Asp Lys Asp Leu Glu Ser Glu Glu Ala
1               5                   10                  15

Leu Trp Asp Leu Tyr Glu Arg Trp Gln Ser Ala His Arg Val Arg Arg
            20                  25                  30

```
His His Ala Glu Lys His Arg Arg Phe Gly Thr Phe Lys Ser Asn Ala
        35                  40                  45

His Phe Ile His Ser His Asn Lys Arg Gly Asp His Pro Tyr Arg Leu
    50                  55                  60

His Leu Asn Arg Phe Gly Asp Met Asp Gln Ala Glu Phe Arg Ala Thr
65                  70                  75                  80

Phe Val Gly Asp Leu Arg Arg Asp Thr Pro Ser Lys Pro Pro Ser Val
                85                  90                  95

Pro Gly Phe Met Tyr Ala Ala Leu Asn Val Ser Asp Leu Pro Pro Ser
            100                 105                 110

Val Asp Trp Arg Gln Lys Gly Ala Val Thr Gly Val Lys Asp Gln Gly
            115                 120                 125

Lys Cys Gly Ser Cys Trp Ala Phe Ser Thr Val Val Ser Val Glu Gly
    130                 135                 140

Ile Asn Ala Ile Arg Thr Gly Ser Leu Val Ser Leu Ser Glu Gln Glu
145                 150                 155                 160

Leu Ile Asp Cys Asp Thr Ala Asp Asn Asp Gly Cys Gln Gly Gly Leu
                165                 170                 175

Met Asp Asn Ala Phe Glu Tyr Ile Lys Asn Asn Gly Gly Leu Ile Thr
            180                 185                 190

Glu Ala Ala Tyr Pro Tyr Arg Ala Ala Arg Gly Thr Cys Asn Val Ala
            195                 200                 205

Arg Ala Ala Gln Asn Ser Pro Val Val Val His Ile Asp Gly His Gln
210                 215                 220

Asp Val Pro Ala Asn Ser Glu Glu Asp Leu Ala Arg Ala Val Ala Asn
225                 230                 235                 240

Gln Pro Val Ser Val Ala Val Glu Ala Ser Gly Lys Ala Phe Met Phe
                245                 250                 255

Tyr Ser Glu Gly Val Phe Thr Gly Glu Cys Gly Thr Glu Leu Asp His
            260                 265                 270

Gly Val Ala Val Val Gly Tyr Gly Val Ala Glu Asp Gly Lys Ala Tyr
            275                 280                 285

Trp Thr Val Lys Asn Ser Trp Gly Pro Ser Trp Gly Glu Gln Gly Tyr
    290                 295                 300

Ile Arg Val Glu Lys Asp Ser Gly Ala Ser Gly Leu Cys Gly Ile
305                 310                 315                 320

Ala Met Glu Ala Ser Tyr Pro Val Lys Thr Tyr Ser Lys Pro Lys Pro
                325                 330                 335

Thr Pro Arg Arg Ala Leu Gly Ala Arg Glu Ser Leu
            340                 345

<210> SEQ ID NO 3
<211> LENGTH: 243
<212> TYPE: PRT
<213> ORGANISM: Hordeum vulgare

<400> SEQUENCE: 3

Val Ser Asp Leu Pro Pro Ser Val Asp Trp Arg Gln Lys Gly Ala Val
1               5                   10                  15

Thr Gly Val Lys Asp Gln Gly Lys Cys Gly Ser Cys Trp Ala Phe Ser
            20                  25                  30

Thr Val Val Ser Val Glu Gly Ile Asn Ala Ile Arg Thr Gly Ser Leu
        35                  40                  45

Val Ser Leu Ser Glu Gln Glu Leu Ile Asp Cys Asp Thr Ala Asp Asn
50                  55                  60
```

```
Asp Gly Cys Gln Gly Gly Leu Met Asp Asn Ala Phe Glu Tyr Ile Lys
 65                  70                  75                  80

Asn Asn Gly Gly Leu Ile Thr Glu Ala Ala Tyr Pro Tyr Arg Ala Ala
                 85                  90                  95

Arg Gly Thr Cys Asn Val Ala Arg Ala Ala Gln Asn Ser Pro Val Val
            100                 105                 110

Val His Ile Asp Gly His Gln Asp Val Pro Ala Asn Ser Glu Glu Asp
        115                 120                 125

Leu Ala Arg Ala Val Ala Asn Gln Pro Val Ser Val Ala Val Glu Ala
        130                 135                 140

Ser Gly Lys Ala Phe Met Phe Tyr Ser Glu Gly Val Phe Thr Gly Glu
145                 150                 155                 160

Cys Gly Thr Glu Leu Asp His Gly Val Ala Val Val Gly Tyr Gly Val
            165                 170                 175

Ala Glu Asp Gly Lys Ala Tyr Trp Thr Val Lys Asn Ser Trp Gly Pro
            180                 185                 190

Ser Trp Gly Glu Gln Gly Tyr Ile Arg Val Glu Lys Asp Ser Gly Ala
        195                 200                 205

Ser Gly Gly Leu Cys Gly Ile Ala Met Glu Ala Ser Tyr Pro Val Lys
        210                 215                 220

Thr Tyr Ser Lys Pro Lys Pro Thr Pro Arg Arg Ala Leu Gly Ala Arg
225                 230                 235                 240

Glu Ser Leu
```